United States Patent [19]

Ziegler

[11] Patent Number: 5,310,556
[45] Date of Patent: May 10, 1994

[54] COSMETIC COMPOSITION

[75] Inventor: Philip D. Ziegler, Oxford, Conn.

[73] Assignee: Chesebrough-Pond's USA Co., Division of Conopco, Inc., Greenwich, Conn.

[21] Appl. No.: 74,184

[22] Filed: Jun. 9, 1993

[51] Int. Cl.$^5$ .............................................. A61K 7/48
[52] U.S. Cl. ....................................... 424/401; 514/78; 514/786; 514/844; 514/846; 514/847; 514/937; 514/938
[58] Field of Search ................... 424/401; 514/78, 786, 514/937, 938, 942, 844, 846, 847, 937, 938; 436/71

[56] References Cited

U.S. PATENT DOCUMENTS 4,537,782 8/1985 Millet et al. .......................... 514/774
4,760,096 7/1988 Sakai et al. ........................... 514/847

FOREIGN PATENT DOCUMENTS

90/01323 2/1990 PCT Int'l Appl. .
2050799 1/1981 United Kingdom .

Primary Examiner—Thurman K. Page
Assistant Examiner—Jyothsna Venkat
Attorney, Agent, or Firm—Milton L. Honig

[57] ABSTRACT

A cosmetic composition is provided having exceptional emulsion stability. The composition includes water, petroleum jelly, a sterol, a phosphatide and a $C_{16}$–$C_{22}$ alkanoic triglyceride.

7 Claims, No Drawings

COSMETIC COMPOSITION

BACKGROUND OF THE INVENTION

1. Field of the Invention

The invention concerns a cosmetic composition in emulsion form.

2. The Related Art

Petroleum jelly, commercially available under the Vaseline ® brand, has long been recognized as therapeutically effective against dry skin. A major negative limiting use of petroleum jelly is the greasiness of this material. Petroleum jelly operates as a barrier but does not penetrate into the skin. Transfer of this material onto clothing, therefore, readily occurs. By contrast, water-based formulations, although often less effective, do not transfer to clothing and exhibit better feel properties. Not surprisingly, water-based cosmetic compositions such as aqueous lotions and creams have garnered the main share of the market.

An approach to providing the benefits of petroleum jelly while neutralizing its greasy feel has been the preparation of aqueous petroleum jelly emulsions. Emulsifiers have been utilized to provide compatibility between aqueous and oil phases. Attempts at emulsification have not always been successful. Even when successful, the resultant product often times fails to exhibit the skin protective properties of petroleum jelly. New and improved emulsifying systems would be highly desirable.

Illustrative of the art is U.S. Pat. No. 4,760,096 (Sakai et al) which discloses a skin moisturizing preparation that includes a phosphatide, at least one $C_{10}$–$C_{30}$ carboxylic acid sterol ester and at least one $C_6$–$C_{12}$ alkanoic triglyceride in a dermatologically acceptable carrier. WO 90/01323 (Bernstein) describes a composition for preventing dry skin based on a lipid concentrate combining three naturally-occurring lipid groups found in the stratum corneum. These groups include fatty acids, sterols (e.g. cholesterol) and sterol esters, and phospholipids and glycolipids (e.g. lecithin and ceramides). U.S. Pat. No. 4,855,090 (Wallach) approaches the problem through the use of liposome technology. A nonaqueous lipophilic phase is combined with an aqueous phase under high shear mixing conditions to form the liposomes. Among the components included in the lipophilic phase are cholesterol and polyoxyethylene fatty ether surfactant while the aqueous phase contains phsophatides such as lecithin.

In this area of technology, further improvements are desirable with respect to skin conditioning and product stability.

Accordingly, it is an object of the present invention to provide a cosmetic composition for skin which exhibits improved moisturization and provides greater protection against dry skin condition.

It is a further object of the present invention to provide a cosmetic composition for skin which has improved storage stability.

These and other objects of the present invention will become more readily apparent from the detailed description and examples which follow.

SUMMARY OF THE INVENTION

A cosmetic composition is provided including:
(i) from about 5 to 80% by weight of water;
(ii) from about 0.5 to 30% by weight of petroleum jelly;
(iii) from about 0.01 to 10% by weight of sterol;
(iv) from about 0.001 to 5% by weight of a phosphatide; and
(v) from about 0.5 to 20% by weight of a $C_{16}$–$C_{22}$ alkanoic triglyceride.

DETAILED DESCRIPTION OF THE INVENTION

The object of the present invention, especially with respect to emulsion stability and skin moisturization, are achieved with a water and oil emulsion that includes petroleum jelly, a sterol, a phosphatide and a $C_{16}$–$C_{22}$ alkanoic triglyceride.

The emulsion will contain water in an amount from about 5 to about 80%, preferably from about 10 to about 50%, optimally between about 20 and 40% by weight of the composition.

A second essential element of the cosmetic composition according to the present invention is petroleum jelly. The amount of petroleum jelly will range from about 0.5 to 30%, preferably between about 3 and 20%, optimally between 5 and 15% by weight.

A third essential element of the cosmetic composition according to the present invention is a sterol. Preferably the sterol is a $3\beta$-sterol having a tail on the 17 position and having no polar groups. Illustrative of this category is cholesterol, sitosterol, stigmasterol and ergosterol. Cholesterol and soy sterol are preferred. A commercial source of soy sterol is a product known as Generol 122 ®, available from the Henkel Corporation, Ambler, Pa. Generol 122 ® is a mixture of stigmasterol, sitosterol and ergosterol. Cosmetic compositions according to the present invention will include the sterol in an amount from about 0.01 to about 10%, preferably between about 0.05 and 2%, optimally between about 0.05 and 1.5% by weight.

A further essential component of the cosmetic composition according to the present invention is a phosphatide. Examples of suitable phosphatides are lecithin, phosphatidyl choline, phosphatidyl ethanolamine, phosphatidyl serine, phosphatidyl inositol, diphosphatidyl glycerol and mixtures thereof. Lysophosphoglycerides may also serve as the phosphatide. Preferred from among the foregoing list is lecithin. Amounts of the phosphatide will range from about 0.001 to 5%, preferably from about 0.01 to 2%, optimally between about 0.025 and 1% by weight.

A further essential component of the cosmetic composition according to the present invention is a $C_{16}$–$C_{22}$ alkanoic triglyceride. Preferably the triglyceride will be based on a material whose major component is linoleic acid residues. Sunflower seed oil is the preferred embodiment. Amounts of the triglyceride will range from about 0.5 to 20%, preferably from about 1 to 15%, optimally between about 2 and 10% by weight.

Another useful ingredient of the cosmetic composition according to the present invention is a gamma-linolenic acid. Borage seed oil (comprising 20% gamma-linolenic acid) is a desirable source for this ingredient. Amounts of the gamma-linolenic acid may range from about 0.001 to 5%, preferably between about 0.01 to 2% by weight.

For improved lubricity, there may also be included one or more silicone oils or fluids which may be selected from a dimethyl polysiloxane, a methylphenyl polysiloxane and an alcohol-soluble silicone glycol copolymer. Preferred siloxanes include diemthyl polysiloxane (CTFA name: dimethicone), a polysiloxane endblocked with trimethyl units and polydimethylcyclosiloxane, (CTFA name: cyclomethicone). The preferred siloxanes exhibit a viscosity from about 2 to 50 centistokes at 25° C. Amounts of the silicones can range from about 0.5 to about 60%, preferably between about 1 and about 30% by weight.

A variety of oily emollients may be employed in the compositions of this invention. These emollients may be selected from hydrocarbon oils (e.g. mineral oil), $C_1$-$C_{20}$ alkyl esters of fatty acids having 10 to 20 carbon atoms, $C_{10}$-$C_{22}$ fatty acids (e.g., stearic, palmitic, myristic and oleic acids), $C_{10}$-$C_{22}$ fatty alcohols (e.g., stearyl, palmityl, lauryl, myristyl and oleyl alcohols), $C_{10}$-$C_{22}$ fatty alcohol ethers formed from ethoxylation of the alcohols with 1-50 ethylene or propylene oxide groups, $C_5$-$C_{50}$ polyhydric alcohol esters and combinations thereof.

Amounts of the above listed emollients may range anywhere from about 0.5 to 40% by weight of the total composition. Preferably the amounts of these emollients will range from about 2 to 25%, optimally between about 5 and 15% by weight.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerin, propoxylated glycerin and mixtures thereof. For best results the humectant is preferably glycerin. The amount of humectant may range anywhere from 0.5 to 20%, preferably between 1 and 15% by weight of the composition.

Sunscreen agents may also be included within compositions of the present invention. The term "sunscreen agent" as used herein defines ultraviolet ray-blocking compounds exhibiting absorption within the wavelength region between 290 and 420 nm. Sunscreens may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides.

The compositions of the invention can also include thickeners/viscosifiers in amounts up to about 5% by weight. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses, and cross-linked acrylic acid polymers such as those sold by B. F. Goodrich under the Carbopol ® trademark.

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable preservatives for compositions of this invention are alkyl esters of para-hydroxybenzoic acid, hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are DMDM hydantoin, methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to 2% by weight of the composition.

Minor adjunct ingredients may also include fragrances, antifoam agents, bacteriostats, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

The following formulation is a cream composition that was prepared with the following ingredients.

| CREAM | |
|---|---|
| INGREDIENT | WEIGHT % RANGE |
| Water | 30-60 |
| Carbopol Dispersion (2% in water) | 10-50 |
| Petroleum Jelly | 5-30 |
| Myreth-3-Myristate | 2-20 |
| Glycerin | 2-20 |
| Sunflower Seed Oil | 0.5-10 |
| Cetearyl Alcohol/Cetyl Steareth 20 | 0.5-10 |
| Triethanolamine | 0.1-5 |
| Dimethicone | 0.1-5 |
| DMDM Hydantoin | 0.05-1 |
| Methyl Paraben | 0.05-1 |
| Propyl Paraben | 0.05-1 |
| Fragrance | 0.05-1 |
| Cholesterol | 0.01-1 |
| Stearic Acid | 0.01-1 |
| Lecithin | 0.01-1 |
| Borage Seed Oil (Gamma-Linolenic Acid) | 0.01-1 |

EXAMPLE 2

The following formulation is a lotion composition that was prepared with the following ingredients.

| LOTION | |
|---|---|
| INGREDIENT | WEIGHT % RANGE |
| Water | 40-80 |
| Glycerin | 1-30 |
| Petroleum Jelly | 1-30 |
| Carbopol Dispersion (2%) | 1-20 |
| Mineral Oil | 0.5-10 |
| Stearic Acid | 0.5-10 |
| Sunflower Seed Oil | 0.5-10 |
| Glycol Stearate | 0.5-10 |
| Cetyl Acetate | 0.5-10 |
| Glycerol Monostearate | 0.5-10 |
| Triethanolamine | 0.5-10 |
| Dimethicone | 0.5-10 |
| POE-40-Stearyl Ether | 0.1-5 |
| Cetyl Alcohol | 0.1-5 |
| Methyl Paraben | 0.5-1 |

-continued

| LOTION | |
|---|---|
| INGREDIENT | WEIGHT % RANGE |
| Propyl Paraben | 0.5-1 |
| Fragrance | 0.5-1 |
| Magnesium Aluminum Silicate | 0.5-1 |
| Cholesterol | 0.01-1 |
| Disodium EDTA | 0.01-1 |
| Lecithin | 0.01-1 |
| DMDM Hydantoin | 0.01-1 |
| Borage Seed Oil (Gamma-Linolenic Acid) | 0.01-1 |
| Ascorbyl Palmitate | 0.0001-0.1 |

EXAMPLE 3

The following formulation is a concentrate composition that was prepared with the following ingredients.

| CONCENTRATE | |
|---|---|
| INGREDIENT | WEIGHT % RANGE |
| Glycerin | 10-50 |
| Carbopol Dispersion (2%) | 10-50 |
| Cyclomethicone | 5-30 |
| Cyclomethicone/Dimethicone | 5-30 |
| Sunflower Seed Oil | 5-20 |
| Petroleum Jelly | 1-20 |
| Oleth-10 | 1-20 |
| Generol 122 ® (Soy Sterol) | 0.5-10 |
| Borage Seed Oil (Gamma-Linolenic Acid) | 0.5-10 |
| Silicone Fluid 350 | 0.5-10 |
| Water | 0.5-10 |
| Stearic Acid | 0.5-10 |
| Lecithin | 0.1-1 |
| Triethanolamine | 0.1-1 |
| Vitamin E Acetate | 0.1-1 |
| Vitamin A Palmitate/Vitamin D3 | 0.1-1 |
| Glydant Plus ® | 0.01-1 |
| Disodium EDTA | 0.01-1 |

EXAMPLE 4

A series of formulations were prepared to evaluate emulsion stabilities of the key components of compositions according to the present invention. These formulations are listed in the Table below.

TABLE

| | Stability of Emulsion | | | | | | |
|---|---|---|---|---|---|---|---|
| | Formulation (wt %) | | | | | | |
| Component | A | B | C | D | E | F | G |
| Water | 80 | 79 | 77 | 77 | 78 | 77 | 77 |
| Petroleum Jelly | 20 | 20 | 20 | 20 | 20 | 10 | 10 |
| Lecithin | — | 1 | 1 | 1 | — | 1 | 1 |
| Generol 122 ® | — | — | 2 | — | 2 | 2 | 2 |
| Cholesterol | — | — | — | 2 | — | — | — |
| Sunflower Seed Oil | — | — | — | — | — | 10 | — |
| Capric/Caprylic/ Triglyceride | — | — | — | — | — | — | 10 |
| Physical Properties of Emulsion | Separation | Separation | Good Emulsion but extremely thick | Good Emulsion but extremely thick | Separation | Good Emulsion and Viscosity | Unstable Emulsion |

Formulations A and B demonstrate that even in the presence of lecithin (emulsifying agent) a combination of water and petroleum jelly exhibit immediate phase separation. Addition of soy sterol or cholesterol, as in Formulations C and D, do allow for the structuring of an emulsion. However, these emulsions were extremely thick and physically unattractive. In the absence of lecithin, but with soy sterol present, Formulation E exhibited phase separation between water and petroleum jelly.

By contrast with Formulations A-E, addition of sunflower seed oil ($C_{16}$-$C_{22}$ alkanoic triglyceride), as shown in Formulation F, achieved an excellent emulsion with good storage stability. Replacement of the sunflower seed oil with caprylic/capric ($C_6$-$C_{12}$ alkanoic) triglyceride (as in Formulation G), provided an emulsion that was only momentarily stable and broke shortly after preparation. These results indicate the criticality of the lecithin, sterol, $C_{16}$-$C_{22}$ alkanoic triglyceride combination for stabilizing a water and petroleum jelly emulsion.

Although this invention is described with reference to specific Examples it will be apparent to one skilled in the art that various modifications may be made thereto which fall within the spirit and purview of this invention.

What is claimed is:

1. A cosmetic composition comprising:
   (i) from about 5 to 80% by weight of water;
   (ii) from about 0.5 to 30% by weight of petroleum jelly;
   (iii) from about 0.01 to 10% by weight of sterol selected from the group consisting of cholesterol, stigmasterol, sitosterol, ergosterol and combinations thereof;
   (iv) from about 0.001 to 5% by weight of lecithin; and
   (v) from about 0.5 to 20% by weight of a $C_{16}$-$C_{22}$ alkanoic triglyceride which is a sunflower seed oil.

2. A composition according to claim 1, further comprising from about 0.001 to about 5% by weight of gamma-linolenic acid.

3. A composition according to claim 1, wherein water is present in an amount from about 10 to 50% by weight.

4. A composition according to claim 1, wherein the petroleum jelly is present in an amount from about 3 to 20% by weight.

5. A composition according to claim 1, wherein the sterol is present in an amount from about 0.05 to 2% by weight.

6. A composition according to claim 1, wherein lecithin is present in an amount from about 0.01 to 2% by weight.

7. A composition according to claim 1, wherein the $C_{16}$-$C_{22}$ alkanoic triglyceride is present in an amount from about 1 to 15% by weight.

* * * * *